(12) United States Patent
Liou et al.

(10) Patent No.: US 9,393,278 B2
(45) Date of Patent: Jul. 19, 2016

(54) METHOD FOR WOUND HEALING

(71) Applicant: HAN SHENG BIOTECH CO., LTD., Pingtung County (TW)

(72) Inventors: Shorong-Shii Liou, Pingtung County (TW); I-Min Liu, Pingtung County (TW); Wei-Cheng Chen, Pingtung County (TW); Ren-Jye Wang, Pingtung County (TW)

(73) Assignee: HAN SHENG BIOTECH CO., LTD., Changjhih Township, Pingtung County (TW)

( * ) Notice: Subject to any disclaimer, the term of this patent is extended or adjusted under 35 U.S.C. 154(b) by 95 days.

(21) Appl. No.: 13/927,598

(22) Filed: Jun. 26, 2013

(65) Prior Publication Data
US 2015/0004263 A1    Jan. 1, 2015

(51) Int. Cl.
*A61K 36/534* (2006.01)
*A61K 36/35* (2006.01)
*A61K 36/355* (2006.01)
*A61K 36/185* (2006.01)

(52) U.S. Cl.
CPC ............. *A61K 36/534* (2013.01); *A61K 36/355* (2013.01)

(58) Field of Classification Search
CPC ................................................ A61K 2300/00
USPC ............................................ 424/725, 195.18
See application file for complete search history.

(56) References Cited

U.S. PATENT DOCUMENTS

| 4,745,098 A | 5/1988 | Michaeli |
| 6,187,743 B1 | 2/2001 | Obi-Tabot |
| 2009/0317474 A1 * | 12/2009 | Van Den Plas et al. ....... 424/487 |

FOREIGN PATENT DOCUMENTS

CN          102940870 A  *  2/2013

OTHER PUBLICATIONS

Zhang et al., "Antimicrobial and Antioxidation Invitro of Chlorogenic Acid in *Flos lonicerae*," J. of Tianjin Univ. of Sci & Tech, vol. 20, No. 2, pp. 5-9 (Jun. 2005) with English Abstract included.

* cited by examiner

*Primary Examiner* — Chris R Tate
*Assistant Examiner* — Randall Winston
(74) *Attorney, Agent, or Firm* — Muncy, Geissler, Olds & Lowe, P.C.

(57) ABSTRACT

A herbal composition for wound healing is disclosed. The herbal composition comprises an extract of honeysuckle and an extract of mint in a weight ration of 1:2 to 2:1. The herbal composition further comprises a medical acceptable excipient.

1 Claim, 2 Drawing Sheets
(1 of 2 Drawing Sheet(s) Filed in Color)

C1

C2

C3

C4

METHOD FOR WOUND HEALING

BACKGROUND OF THE INVENTION

1. Field of the Invention

The present invention relates to a composition and, more particularly, to a herbal composition for wound healing. The present invention further relates to a method for wound healing by administrating the herbal composition to a target in need.

2. Description of the Related Art

Wounds comprising crush wounds, cuts, incisions, squeeze wounds, stab wounds or wounds due to surgery, plastic surgery or chronic disease have demands of wound healing. In particular, wounds with large area on body surface incur a huge time and cost in medical care, further impair mobility and diminish quality of life of victims.

Normal wound healing is divided into four sequential, yet overlapping, phases including hemostatic phase, inflammatory phase, proliferative phase and remolding phase. In the early period of wound healing, several factors, such as inflammation caused by wound infection, surface humidity, vertilativity of wound are important for improving wound healing.

Collagen is usually used as an active substance in a conventional composition for wound healing. Collagen is an intrinsic ingredient of organisms with advantages of excellent biocompatibility, biodegradability and low immunity. However, collagen has limited anti-inflammation ability. Moreover, collagen from animal tissues is associated with a great risk of disease transmission. In contrast, collagen manufactured by genetic engineering provides an excellent safety profile concerning the risk of disease transmission, but has a bottleneck lying in difficulties in obtaining collagens with natural structure, thereby increasing cost of the conventional composition for wound healing.

SUMMARY OF THE INVENTION

It is therefore the objective of this invention to provide a herbal composition which inhibits wound inflammation and enhances wound healing.

It is another objective of this invention to provide a method for wound healing, thereby decreasing healing time of wounds and diminishing cost of medical care.

A herbal composition comprises an extract of honeysuckle and an extract of mint in a weight ratio of 1:2 to 2:1, and more particularly, the weight ratio of the extract of honeysuckle and the extract of mint is 1:1.

In a preferred form shown, the extract of honeysuckle is an ethanolic extract via 50% ethanol and the extract of mint is a water extract of mint.

In a preferred form shown, the herbal composition further comprises a medical acceptable excipient.

In a preferred form shown, the herbal composition comprises 5 wt % of the extract of honeysuckle and 5 wt % of the extract of mint.

In a preferred form shown, the medical acceptable excipient is a polyethylene glycol with molecular weight between 200 and 10,000 kDa.

A method for wound healing comprises administrating an effective amount of the herbal composition to a target in need thereof, wherein the herbal composition comprises an extract of honeysuckle and an extract of mint in a weight ratio of 1:2 to 2:1.

In a preferred form shown, the effective amount of the herbal composition is 0.75 kg/per m² of wound area.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
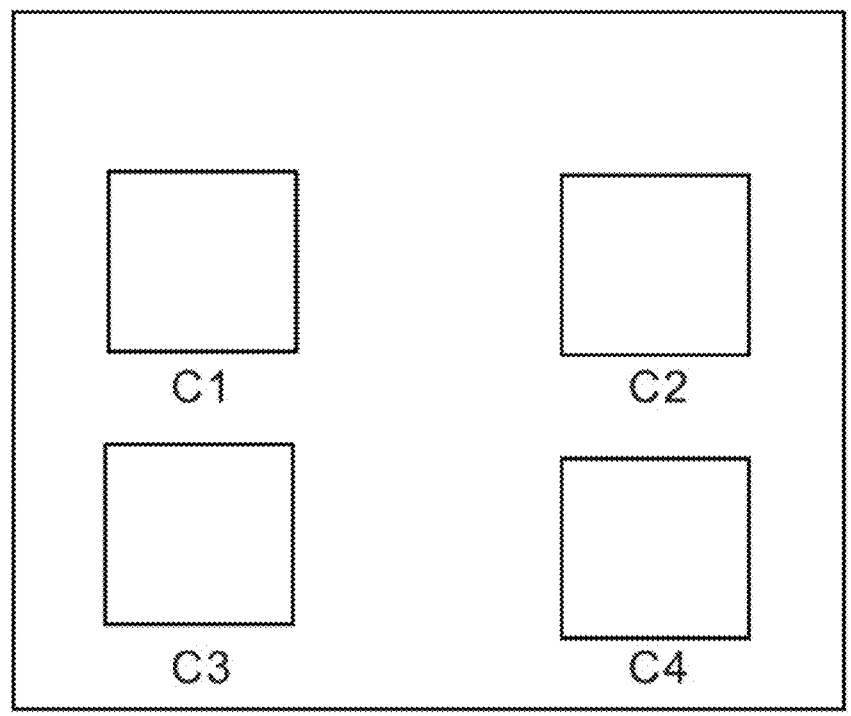
FIG. 1 depicts a schematic illustration of wound healing experiment.

An embodiment of a herbal composition according to preferred teachings of the present invention comprises: an extract of honeysuckle and an extract of mint in a weight ratio of 1:2 to 2:1, and more particularly, the weight ratio of the extract of honeysuckle and the extract of mint is 1:1.

In the embodiment, honeysuckle indicates *Lonicera japonica* Thunb. which belongs to *Caprifloiaceae Lonicera*. Honeysuckle poses activities of anti-bacteria, anti-inflammatory, cooling of fever and enhancing phagocytosis of phagocytes. In addition, non-limiting examples of honeysuckle includes its roots, stems, leaves, flowers and flower buds.

Furthermore, in the embodiment, mint indicates plant which belongs to *Lamiaceae Mentha*. Mint poses activities of inhibition of various viruses and bacteria. Moreover, non-limiting examples of mint includes its roots, stems, leaves or entire plants of *Mentha arvensis, Mentha canadensis, Mentha aquatica, Metha piperita* var "chocolate", *Mentha pulegium, Mentha×gracilis, Mentha×piperita* "Swiss" and *Mentha piperita*.

In the embodiment, flower buds of honeysuckle (*Lonicera japonica* Thunb. from Taiwan) and entire plants of mint (*Mentha arvensis* from Taiwan) are used. Honeysuckle is extracted by 50% ethanol to obtain an ethanolic extract of honeysuckle and mint is extracted by RO water to obtain a water extract of mint. In detail, in this embodiment, honeysuckle and mint are extracted under 45 to 55□ using vibrating with 200 rpm for 8 hours to obtain two extracted mixtures. Then, the two extracted mixtures are filtered, vacuum concentrated and freeze-dried to obtain the ethanolic extract of honeysuckle and the water extract of mint, respectively. Furthermore, the ethanolic extract of honeysuckle and the water extract of mint are mixed in a weight ratio of 1:2 to 2:1 to obtain the herbal composition of the invention.

In order to understand whether the herbal composition of the invention is capable of elevating anti-oxidant activity, thereby scavenging free radicals effectively, free radicals scavenging rates are measured as follows:

(A) Reduction of DPPH Free Radical

As shown in Table 1, the herbal composition of the invention (groups A1 to A3), extracts of honeysuckle or mint by RO water, 50% ethanol or 95% ethanol, respectively (groups A4 to A9) are used as samples in the experiment. 1 mL of DPPH (α,α-diphenyl-β-picrylhydrazyl), 0.95 mL Tris-HCl buffer and the samples with concentrations of 31.25, 62.5, 125, 250, 500, 1000, 2000 and 3000 μg/mL are mixed, respectively. Each mixture containing DHHP, Tris-HCl buffer and the sample is then vortexed vigorously for 20 seconds, followed by standing for 30 minutes at room temperature. The absorbance is measured at 517 nm. The DPPH free radical scavenging rate is calculated in the following formulation:

% of DPPH scavenging=[1−(sample absorbance/control absorbance)]×100%

TABLE 1

Half maximal inhibitory concentration ($IC_{50}$) of the samples

| Groups | Sample | $IC_{50}$ (μg/mL) |
|---|---|---|
| A1 | the herbal composition of the invention with honeysuckle and mint in a weight ration of 1:1 | 0.43 ± 0.06 |
| A2 | the herbal composition of the invention with honeysuckle and mint in a weight ration of 2:1 | 0.49 ± 0.08 |
| A3 | the herbal composition of the invention with honeysuckle and mint in a weight ration of 1:2 | 0.45 ± 0.04 |
| A4 | the extract of honeysuckle by RO water | 1.23 ± 0.07 |
| A5 | the extract of honeysuckle by 50% ethanol | 0.82 ± 0.09 |
| A6 | the extract of honeysuckle by 95% ethanol | 1.97 ± 0.11 |
| A7 | the extract of mint by RO water | 0.52 ± 0.03 |
| A8 | the extract of mint by 50% ethanol | 1.43 ± 0.06 |
| A9 | the extract of mint by 95% ethanol | 1.82 ± 0.08 |

Referring to Table 1, in groups A4 to A6, DPPH scavenging ability is in a order of A5 ($IC_{50}$: 0.82±0.09 μg/mL, by 50% ethanol)>A4 ($IC_{50}$: 1.23±0.07 μg/mL, by RO water)>A6 ($IC_{50}$: 1.97±0.11 μg/mL, by 95% ethanol). In groups A7 to A9, DPPH scavenging ability is in a order of A7 ($IC_{50}$: 0.52±0.03 μg/mL, by RO water)>A8 ($IC_{50}$: 1.43±0.06 μg/mL, by 50% ethanol)>A9 ($IC_{50}$: 1.82±0.08 μg/mL, by 95% ethanol). In groups A1 to A3, DPPH scavenging ability is in a order of A1 ($IC_{50}$: 0.43±0.06 μg/mL, with honeysuckle and mint in a weight ration of 1:1)>A3 ($IC_{50}$: 0.45±0.04 μg/mL, with honeysuckle and mint in a weight ration of 1:2)>A2 ($IC_{50}$: 0.49±0.08 μg/mL, with honeysuckle and mint in a weight ration of 2:1). Furthermore, the herbal composition of the invention has a lower $IC_{50}$ compared with single extracts of honeysuckle and mint, indicating the herbal composition of the invention has a better DHHP free radical scavenging ability.

(B) Reduction of Superoxide Anion Free Radical

As shown in Table 2, the herbal composition of the invention (groups B1 to B3), extracts of honeysuckle or mint by RO water, 50% ethanol or 95% ethanol, respectively (groups B4 to B9) are used as samples in the experiment. Equal volume of PMS (phenazine methosulphat), NADH (nicotinamide adenine dinucleotide), NBT (dihidromicotineamidadenibe dinucleotide) and the samples with concentrations of 31.25, 62.5, 125, 250, 500, 1000, 2000 and 3000 μg/mL are mixed, respectively. Each mixture containing PMS, NADH, NBT and the sample is then standed for 5 minutes at room temperature. The absorbance is measured at 560 nm. The superoxide anion free radical scavenging rate is calculated in the following formulation:

% of superoxide anion scavenging=[1−(sample absorbance/control absorbance)]×100%

TABLE 2

Half maximal inhibitory concentration ($IC_{50}$) of the samples

| Groups | Sample | $IC_{50}$ (μg/mL) |
|---|---|---|
| B1 | the herbal composition of the invention with honeysuckle and mint in a weight ration of 1:1 | 0.57 ± 0.08 |
| B2 | the herbal composition of the invention with honeysuckle and mint in a weight ration of 2:1 | 0.59 ± 0.07 |
| B3 | the herbal composition of the invention with honeysuckle and mint in a weight ration of 1:2 | 0.60 ± 0.05 |
| B4 | the extract of honeysuckle by RO water | 1.44 ± 0.07 |
| B5 | the extract of honeysuckle by 50% ethanol | 0.63 ± 0.06 |
| B6 | the extract of honeysuckle by 95% ethanol | 0.92 ± 0.06 |
| B7 | the extract of mint by RO water | 0.75 ± 0.04 |
| B8 | the extract of mint by 50% ethanol | 2.06 ± 0.14 |
| B9 | the extract of mint by 95% ethanol | 2.13 ± 0.11 |

Referring to Table 2, in groups B4 to B6, superoxide anion scavenging ability is in a order of B5 ($IC_{50}$: 0.63±0.06 μg/mL, by 50% ethanol)>B6 ($IC_{50}$: 0.92±0.06 μg/mL, by 95% ethanol)>B4 ($IC_{50}$: 1.44±0.07 μg/mL, by RO water). In groups B7 to B9, superoxide anion scavenging ability is in a order of B7 ($IC_{50}$: 0.75±0.04 μg/mL, by RO water)>B8 ($IC_{50}$: 2.06±0.14 μg/mL, by 50% ethanol)>B9 ($IC_{50}$: 2.13±0.11 μg/mL, by 95% ethanol). In groups B1 to B3, superoxide anion scavenging ability is in a order of B1 ($IC_{50}$: 0.57±0.08 μg/mL, with honeysuckle and mint in a weight ration of 1:1)>B2 ($IC_{50}$: 0.59±0.07 μg/mL, with honeysuckle and mint in a weight ration of 2:1)>B3 ($IC_{50}$: 0.60±0.05 μg/mL, with honeysuckle and mint in a weight ration of 2:1). Furthermore, the herbal composition of the invention has a lower $IC_{50}$ compared with single extracts of honeysuckle and mint, indicating the herbal composition of the invention has a better superoxide anion free radical scavenging ability.

As a whole, the herbal composition of the invention has a better free radical scavenging ability compared with single extracts of honeysuckle and mint.

In order to understand whether the herbal composition of the invention is capable of reducing wound inflammation causing by free radicals, thereby enhancing wound healing, the extract of honeysuckle and the extract of mint are mixed with a medical acceptable excipient.

In detail, the medical acceptable excipient is selected from a group of dispersants, electrolytes, penetrants, softeners, pH buffers, surfactants, improvers, solubilizers, stabilizers and lubricants. Preferably, the medical acceptable excipient is a polyethylene glycol (PEG) with molecular weight between 200 and 10,000 kDa. In the embodiment, the herbal composition of the invention comprises 5 wt % of the extract of honeysuckle, 5 wt % of the extract of mint, 40 wt % of PEG 6000, 25 wt % of PEG 4000 and 25 wt % of RO water. After thoroughly mixing the components mentioned above, the herbal composition is dissolved in a water-jacketed boiler of 70□, followed by cooling at room temperature to obtain the herbal composition of the invention as a paste form.

(C) Enhancing of Wound Healing

Wistar male rats (8 week-old) purchased from the animal center of the National Laboratory Animal Center (NLAC, Taiwan) are used in this experiment. The rats are singly housed in microisolator cages and kept on free diet and water. On day 0, the rats are anaesthetized and four single standardized full thickness wound with 2 cm of length, 2 cm of width and 0.5 cm of depth are created in the dorsal skin of each rats, as shown in FIG. 1. Immediately, after wounding (day 0) are subsequently on days 3, 6, 9, 12 and 15, all the wounds are digitally photographed, and wound area are measured by tracing the wound margins and the surface area is calculated More particularly, samples such as a collagen paste (containing 10 wt % collagen, group C1), a honeysuckle paste (containing 10 wt % honeysuckle, group C2), a mint paste (containing 10 wt % mint, group C3) and the herbal composition of the invention (containing 5 wt % of honeysuckle and 5 wt % of mint, group C4) are administered to the four wounds created in the dorsal skin of each rats, respectively.

In the embodiment, 0.3 g of the samples of groups C2 to C4 are administered at AM 9:00 daily. The wounds administered the samples of groups C1 to C4 are wrapped with bandages. Wound healing is calculated in the following formulation:

% of wound healing=[area (day 0)/area (day $X$)]/area (day 0)×100%

TABLE 3

Wound healing of the samples at different time points

| Groups | Days of wound healing (day) | | | | |
|---|---|---|---|---|---|
| | Day 3 | Day 6 | Day 9 | Day 12 | Day 15 |
| C1 | 9.5 ± 3.3 | 15.1 ± 3.9 | 38.2 ± 4.1 | 43.8 ± 3.8 | 57.7 ± 3.2 |
| C2 | 19.1 ± 3.7 | 33.2 ± 3.3 | 55.6 ± 4.8 | 76.9 ± 4.2 | 88.4 ± 3.9 |
| C3 | 18.6 ± 4.3 | 28.7 ± 3.9 | 47.6 ± 5.2 | 68.4 ± 4.7 | 80.3 ± 3.9 |
| C4 | 21.6 ± 4.6 | 40.1 ± 4.1 | 63.1 ± 5.8 | 81.5 ± 3.7 | 95.3 ± 2.6 |

Referred to Table 3, on day 3, group C1 has a wound healing rate of 9.5±3.3%, and groups C2 to C4 have wound healing rates near 20% without significant difference. On day 9, group C4 has a wound healing rate up to 63% (1.6 fold of group C1), and better than groups C2 and C3. On day 12, group C1 has a wound healing rate of 43.8±3.8%, groups C2 and C3 have wound healing rates of 76.9±4.2% and 68.4±4.7%, respectively, while group C4 has a wound healing rate of 81.5±3.7%. On day 15, groups C1 to C3 have wound healing rates of 57.7±3.2%, 88.4±3.9% and 80.3±3.9%, respectively. At the same time, group C4 has a wound healing rate up to 95.3±2.6%, indicating that the wound is almost healed. Therefore, the herbal composition of the invention is capable of enhancing wound healing and shortening time of wound healing. Thus is, a proper ratio of honeysuckle and mint provides a synergic effect on wound healing.

Figure 2:
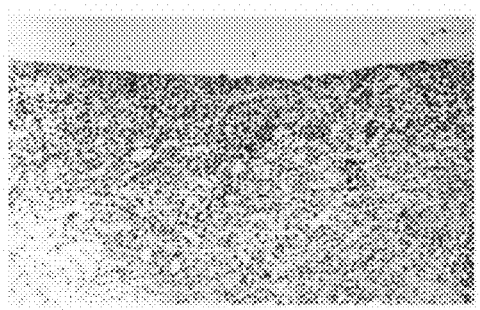
FIG. 2 depicts microscopy images of Hematoxyllin & Eosine (H&E) staining of tissue section derived from rats
Figure 2:
Figure 2:
Figure 2:

Furthermore, on day 9, after anaesthetization, the histological samples for analysis are obtained from a tissue flat that comprised the entire wound bed and underlying tissues, including the dorsal muscular layer. Cross-section specimens with 5 mm in thickness are fixed overnight in 10% formalin and embedded in paraffin for section. Subsequently, Hematoxylin & Eosin staining analysis is performed, and the results are shown in FIG. 2.

Moreover, a semi-quantification process is used in order to evaluate the effect of the herbal composition of the invention on inflammation, proliferation of collagen and regeneration of epidermal cells, recording as wound scores in Table 4.

TABLE 4

Wound scores of the samples

| Groups | Wound scores | | |
|---|---|---|---|
| | Inflammation | Proliferation of collagen | Regeneration of epidermal cells |
| C1 | 4.6 | 2.2 | 2.1 |
| C2 | 3.5 | 2.6 | 3.7 |
| C3 | 3.8 | 2.8 | 3.0 |
| C4 | 3.1 | 3.2 | 4.2 |

In table 4, the wound score of inflammation is a 5-point scale based on the ratio of the inflamed cells in the wound site and a lower number indicated better healing. "1" refers to the ratio of the inflamed cells smaller than 1% (best healing). "2" refers to the ratio of the inflamed cells ranged from 1% to 25%. "3" refers to the ratio of the inflamed cells ranged from 26% to 30%. "4" refers to the ratio of the inflamed cells ranged from 51% to 75%. "5" refers to the ratio of the inflamed cells ranged from 76% to 100% (worst healing).

Furthermore, the wound scores of proliferation of collagen and regeneration of epidermal cells are also 5-point scales based on the ratio of collagens or the epidermal cells in the wound site and a higher number indicated better healing. "1" refers to the ratio of collagens or the epidermal cells smaller than 1% (worst healing). "2" refers to the ratio of collagens or the epidermal cells ranged from 1% to 25%. "3" refers to the ratio of collagens or the epidermal cells ranged from 26% to 30%. "4" refers to the ratio of collagens or the epidermal cells ranged from 51% to 75%. "5" refers to the ratio of collagens or the epidermal cells ranged from 76% to 100% (best healing).

Referred to FIG. 2 and Table 4, group C1 has a significant inflammation in the wound site and a slight proliferation of collagen and regeneration of epidermal cells. Groups C2 and C3 effectively suppress inflammation in the wound site and promote proliferation of collagen and regeneration of epidermal cells. Furthermore, group C4 has a better effect than groups C2 and C4 on either suppression in inflammation or promoting of proliferation of collagen and regeneration of epidermal cells.

Free radicals deprave local inflammation and further obstruct wound healing. The herbal composition of the invention is a free radicals scavenger, thereby effectively suppressing inflammation in the wound site, and accelerating proliferative phase and remolding phase of wound healing. Therefore, the herbal composition of the invention is capable of decreasing healing time of wounds and diminishing cost of medical care.

The herbal composition of the invention may be administered locally or topically to wounds of a target in need with an effective amount of the herbal composition of the invention wherein the effective amount of the herbal composition of the invention is 0.75 kg/per $m^2$ of wound area. The herbal composition of the invention can improve wound healing wherein the wounds are caused by physical, chemical or mechanical damages including, but not limited to, crush wounds, cuts, incisions, squeeze wounds, stab wounds or wounds due to surgery, plastic surgery or chronic disease have demands of wound healing.

The herbal composition of the invention may be delivered via a variety of means, for example via a spray, suspension, cream, lotion, emulsion, gel, liquid aerosol, powder aerosol, drops, endoscopically or antimicrobial dressing such a bandages.

In summary, the herbal composition of the invention is capable to serve as an active ingredient effectively decreasing free radicals in the wound site and suppressing inflammation in the wound site.

Furthermore, the method for wound healing of the invention can effectively diminishing inflammation caused by wound infection, thereby decreasing healing time of wounds and diminishing cost of medical care.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating a wounded area in a subject in need thereof comprising topically administering an effective amount of an herbal composition to the wounded area,
wherein said herbal composition consists of 5 wt % of an extract of *Lonicera japonica* Thunb.; 5 wt % of an extract of *Mentha;* 40 wt % of a polyethylene glycol having a molecular weight of 6000 kDa; 25 wt % of a polyethylene glycol having a molecular weight of 4000 kDa; and 25 wt % of water;
wherein the effective amount of said herbal composition is 0.75 kg/per m$^2$ of the wounded area.

* * * * *